(12) United States Patent
Anderson et al.

(10) Patent No.: US 6,518,245 B1
(45) Date of Patent: Feb. 11, 2003

(54) TREATMENT OF ARRHYTHMIAS VIA INHIBITION OF A MULTIFUNCTIONAL CALCIUM/CALMODULIN-DEPENDENT PROTEIN KINASE

(75) Inventors: Mark E. Anderson, Nashville, TN (US); Andrew P. Braun, Calgary (CA); Howard Schulman, Palo Alto, CA (US); Ruey J. Sung, Hillsborough, CA (US)

(73) Assignee: The Board of Trustees of the Leland Stanford Jr. University, Palo Alto, CA (US)

( * ) Notice: Subject to any disclaimer, the term of this patent is extended or adjusted under 35 U.S.C. 154(b) by 0 days.

(21) Appl. No.: 09/016,145

(22) Filed: Jan. 30, 1998

Related U.S. Application Data
(60) Provisional application No. 60/036,833, filed on Jan. 31, 1997.

(51) Int. Cl.⁷ .......................... A61K 38/10; A61K 31/18
(52) U.S. Cl. .......................... 514/14; 514/601; 514/602; 514/604; 530/327; 564/1; 564/80; 564/84; 564/90; 564/91
(58) Field of Search ................................ 514/601, 602, 514/604, 14; 564/1, 80, 84, 90, 91; 530/327

(56) References Cited

U.S. PATENT DOCUMENTS

| | | | | |
|---|---|---|---|---|
| 4,860,749 A | * | 8/1989 | Lehmann | 128/419 |
| 4,880,005 A | * | 11/1989 | Pless et al. | 128/419 |
| 5,089,526 A | * | 2/1992 | Simon et al. | 514/65 |
| 5,597,848 A | * | 1/1997 | Ito et al. | 514/539 |

FOREIGN PATENT DOCUMENTS

| | | |
|---|---|---|
| EP | 0 368 233 A | 5/1990 |

OTHER PUBLICATIONS

Berkow et al. "Merck Manual of Diagnosis and Therapy", Merck Sharp & Dohme Research Laboratories, pp. 475–477, 1992.*
File CAplus on STN, No. 122:314463. Hidaka et al. JP 06293730. Abstract only, 1995.*
File CAplus on STN, No. 114:159690. Yasugawa et al. 'Autophosphorylation of Calcium/Calmodulin Dependent Protein Kinase II: Effects on Interaction Between Enzyme and Substrate', Jpn. J. Pharmacology, vol. 55, No. 2, pp. 263–274. abstract only, 1991.*
File CAplus on STN, No. 109:142429. Meerson et al. 'Prevention of Ischemic and Reperfusion Arrhythmias with Calmodulin Blocker, Trifluperazine,' Kardiologiya. vol. 28, No. 5, pp. 91–95, 1988.*
Berkow et al. Merck Manual of Diagnosis and Therapy, Merck Sharp & Dohme Research Laboratories, pp. 479–480, 1992.*
Ishikawa et al. 'Effect of New CA+ 2–Calmodulin–Dependent Protein Kinase II Inhibitor on Gaba Release in Cerebrospinal Fluid of the Rat', J. of Pharm. and Exp. Ther. vol. 254, No. 2, pp. 598–602, 1990.*
File Caplus on STN, DN No. 121:277477. Okakazi et al. 'KN–62, a specific Ca+ /calmodlulin–dependent protien kinase inhibitor, reversibly depresses teh rate of beating of cultured fetal mouse cardiac myocytes' J. Pharmacol. Exp. Thr. vol. 270, No. 3, pp., 1994.*
Berkow et al. Merck Manual of Diagnosis and Tehrapy, Merck Sharp & Dhome Research Laboratories pp. 460–475 (1992).*
File Medline on STN. AN No. 77049877. Matsubara et al. "Experimental Anti Arrhythmic Effects of a New Beta Adrnergic Receptor Agent, dl–I–(tert. butylamino)–3–[(2–propinyloxy)phenoxy]2–propanol hydrochloride (dl Ko 1400–Cl). " Nippon Yakurigaku Zasshi. Folia pharmacologica Japonica (Jul. 1976) vol. 72, No. 5, pp. 557–571. Abstract only.*
File Toxlit on STN. DN No. CA–114–156919Q. Cheng et al. "Effects of a New Intracellular Calcium Antagonist, KT–362, on Delayed Afterdepolarization oand Triggered Activity in Guinea Pig Ventricular Myocardium" Yakuri to Chiryo. vol. 18, Supp. 13, p. s5313–s3514. Abstract Only. (1990).*
Ellenbogen et al. "Safety and Efficacy of Intravenous Diltiazem in Atrial Fibrillation or Atrial Flutter", The American Journal of Cardiology 75:45–49 (Jan. 1, 1995).
Goldenberg et al. "Intravenous Diltiazem for the Treatment of Patients with Atrial Fibrillation or Flutter and Moderate to Severe Congestive Heart Failure" The American Journal of Cardiology 74:884–889 (Nov. 1, 1994).
Ishida et al. "Inactivation of $Ca^{2+}$/Calmodulin–Dependent Protein Kinase II by $Ca^{2+}$/Calmodulin" Journal of Biochemistry 115(6):1075–1082 (1994).
Ishikawa et al. "Effect of a New $Ca^{2+}$–Calmodulin–Dependent Protein Kinase II Inhibitor on GABA Release in Cerebrospinal Fluid of the Rat" The Journal of Pharmacology and Experimental Therapeutics 254(2):598–602 (1990).
Levin et al. "Mechanism by Which Psychotropic Drugs Inhibit Adenosine Cyclic 3',5'–Monophosphate Phosphodiesterase of Brain" Molecular Pharmacology 12:581–589 (1976).

(List continued on next page.)

*Primary Examiner*—Brenda Brumback
*Assistant Examiner*—Anish Gupta
(74) *Attorney, Agent, or Firm*—Townsend and Townsend and Crew LLP (57) ABSTRACT

This invention provides a method for treating or preventing arrhythmias in a human subject comprising the administration of an effective amount of a calcium/calmodulin-dependent protein kinase inhibitor. Also provided are pharmaceutical compositions comprising a calcium/calmodulin-dependent protein kinase inhibitor and a pharmaceutically acceptable carrier and methods for identifying agents useful for the treatment of arrhythmias.

32 Claims, 7 Drawing Sheets

OTHER PUBLICATIONS

Okazaki et al. "KN–62, a Specific $Ca^{++}$/ Calmodulin–Dependent Protein Kinase Inhibitor, Reversibly Depresses the Rate of Beating of Cultured Fetal Mouse Cardiac Myocytes " The Journal of Pharmacology and Experimental Therapeutics 270(3):1319–1324 (1994).

Prozialeck et al. "Photoaffinity Labeling of Calmodulin by Phenothiazine Antipsychotics" Molecular Pharmacology 19:264–269 (1981).

Rich et al. "Substrate–directed Function of Calmodulin in Autophosphorylation of $Ca^{2+}$/Calmodulin–dependent Protein Kinase II" The Journal of Biological Chemistry 273(43):28424–28429 (Oct. 23, 1998).

Roufogalis "Phenothiazine Antagonism of Calmodulin: A Structurally–Nonspecific Interaction" Biochemical and Biophysical Research Communications 98(3):607–613 (Feb. 12, 1981).

Schaffer et al. "Phenothiazine Protection in Calcium Overload–Induced Heart Failure: A Possible Role For Calmodulin" The American Physiological Society H328–H334 (1983).

Tokumitsu et al. "KN–62, 1–[N,O–Bis(5–isoquinolinesulfonyl)–N–methyl–L–tyrosyl]–4–phenylpiperazine, a Specific Inhibitor of $Ca^{2+}$/Calmodulin–dependent Protein Kinase II" The Journal of Biological Chemistry 265(8):4315–4320 (Mar. 15, 1990).

Waxman et al. "Verapamil for Control of Ventricular Rate in Paroxysmal Supraventricular Tachycardia and Atrial Fibrillation or Flutter" Annals of Internal Medicine 94(1):1–6 (1/81).

Weiss et al. "Interaction of Calmodulin with Psychotropic Drugs: Neuropsychopharmacological Implications" Psychopharmacology Bulletin 19(3)378–386 (1983).

Weiss et al. "Interaction of Drugs with Calmodulin: Biochemical, Pharmacological and Clinical Implications" Biochemical Pharmacology 31(13):2217–2226 (1982).

Weiss et al. "Mechanism for Selectively Inhibiting the Activation of Cyclic Nucleotide Phosphodiesterase and Adenylate Cyclase by Antipsychotic Agents" Advances in Cyclic Nucleotide Research 9:285–303 (1978).

Anderson et al., "Multifunctional $Ca^{2+}$/Calmodulin–Dependent Protein Kinase Mediates $Ca^{2+}$/Induced Enhancement of the L–type $Ca^{2+}$Current in Rabbit Ventricular Myocytes," Circ. Res., 75:854–861 (1994).

Berkow et al., "Merck Manual of Diagnosis and Therapy," Merck Sharp & Dohme Research Laboratories, 439–442 (1987).

Braun et al., "The Multifunctional Calcium/Calmodulin–Dependent Protein Kinase: From Form to Function," Annual Review of Physiology, 57:417–445 (1995).

Braun et al., "A Non–Selective Cation Current Activated via the Multifunctional $Ca^{2+}$–Calmodulin–Dependent Protein Kinase in Human Epithelial Cells," Journal of Physiology, 488:37–55 (1995).

De Koninck et al., "Sensitivity of CaM Kinase II to the Frequency of Ca2+ Oscillations," Science, 279:227–230 (1998).

Lee et al., "Effect of Ischemia on Calcium–Dependent Fluorescence in Rabbit Hearts Containing Indo 1," Circulation, 78:1047–1059 (1988).

Li et al., "The Effect of $Ca^{2+}$–Calmodulin–Dependent Protein Kinase II on Cardiac Excitation–Contraction Coupling in Ferret Ventricular Myocytes," Journal of Physiology, 501:17–31 (1997).

Sumi et al., "The Newly Synthesized Selective $Ca^{2+}$/Calmodulin Dependent Protein Kinase II Inhibitor KN–93 Reduces Dopamine Contents in PC12h Cells," Biochem. Biophys. Res. Comm., 181:968–975 (1991).

Thandroyen et al., "Intracellular Calcium Transients and Arrhythmia in Isolated Heart Cells," Circ. Res., 69:810–819 (1991).

Tieleman et al., "Verapamil Reduces Tachydcardia–induced Electrical Remodeling of the Atria," Circulation, 95:1945–1953 (1997).

Anderson et al., "A Role for L–Type Calcium Current, Calmodulin, and Multifunctional Calcium/Calmodulin–Dependent Protein Kinase in Early After Depolarizations," NASPE Abstracts & Program, 19:685 (1996).

Anderson et al., "Early Afterdepolarizations Due to L–Type Ca2+ Current are Suppressed by Inhibition of the Multifunctional Ca2+/Calmodulin–Dependent Protein Kinase in Rabbit Myocardium," American Heart Association 69th Scientific Sessions, Nov., 1996.

De Ferrari et al, "Distinct Patterns of Calcium Transients During Early and Delayed Afterdepolarizations Induced by Isoproterenol in Ventricular Myocytes," Circ., 91:2510–2515 (1995).

Enslen et al., "Characterization of $Ca^{2+}$/Calmodulin–Dependent Protein Kinase IV," The Journal of Biological Chemistry, 269:15520–15527 (1994).

Griffith et al., "Inhibition of Calcium/Calmodulin–Dependent Protein Kinase in Drosophila Disrupts Behavioral Plasticity," Neuron, 10:501–509 (1993).

* cited by examiner

TREATMENT OF ARRHYTHMIAS VIA INHIBITION OF A MULTIFUNCTIONAL CALCIUM/CALMODULIN-DEPENDENT PROTEIN KINASE

This application claims priority from provisional application Ser. No. 60/036,833, filed Jan. 31, 1997, under 35 USC §119(e)(1).

BACKGROUND OF THE INVENTION a) Field of the Invention

The present invention relates to methods for the treatment of arrhythmias by inhibition of a multifunctional calcium/calmodulin-dependent protein kinase (CaM kinase), pharmaceutical compositions useful in such treatments, and methods for identifying new agents useful for such treatments.

b) Description of Related Art

Arrhythmias are a leading cause of cardiac-related death in the United States. Prolongation of the cardiac action potential is an important predisposing condition for these arrhythmias. Many antiarrhythmic drugs directly prolong the action potential duration and so may further contribute to these arrhythmias (i.e. the proarrhythmic effects of antiarrhythmic drugs). Despite their cost, implantable cardiac defibrillators (ICDs) have become the treatment of choice for arrhythmias. In order to prevent painful shocks ~50% of patients with ICDs require additional treatment with antiarrhythmic drugs. Thus there is an important need to develop better antiarrhythmic drug therapies.

Early afterdepolarizations (EADs) are depolarizing oscillations in the action potential (AP) that occur during repolarization. One cause of EADs is inward L-type $Ca^{2+}$ current ($I_{Ca}$). $I_{Ca}$ is present at cell membrane potentials (Vm) within the window of $I_{Ca}$ steady state activation and inactivation overlap; such as occur during action potential repolarization. Prolongation of action potential repolarization may increase the time that the Vm is in the window current range for $I_{Ca}$ and thus the likelihood of EADs. EADs are important because they are one probable cause of lethal arrhythmias associated with long QT intervals including torsade de pointes. A long QT interval reflects prolonged action potential repolarization in ventricular myocardium and is due to a wide variety of conditions including bradycardia and hypokalemia. One important cause of long QT intervals are antiarrhythmic drugs and the ventricular proarrhythmic effects of many antiarrhythmic agents are due to QT interval prolongation.

Intracellular $Ca^{2+}$ increases simultaneously with EADs in isolated ventricular myocytes (De Ferrari et al. (1995) *Circ* 91:2510–2515). Elevation of intracellular $Ca^{2+}$ ($[Ca^{2+}]_i$) has complex effects on $I_{Ca}$ including indirect enhancement through a multifunctional $Ca^{2+}$/calmodulin-dependent protein kinase II pathway (Anderson et al. (1994) *Circ Res* 75:854–861) and direct inactivation. The net effect of elevated $[Ca^{2+}]_i$ in rabbit ventricular myocytes following flash photolysis of the photolabile $Ca^{2+}$ chelator Nitr–5 is 40–50% augmentation of peak $I_{Ca}$ that is mediated by a multifunctional $Ca^{2+}$/calmodulin-dependent protein kinase II, hereafter referred to as CaM kinase II. CaM kinase II, like other multifunctional $Ca^{2+}$/calmodulin-dependent protein kinases, is an ubiquitous serine-threonine kinase that is activated when $Ca^{2+}$ is bound to the $Ca^{2+}$ binding protein calmodulin. Once activated by $Ca^{2+}$/calmodulin, CaM kinase II activation may be sustained by intersubunit enzyme autophosphorylation that confers $Ca^{2+}$-independent activity, allowing for its activity to persist during the long diastolic intervals associated with QT interval prolongation and torsade de pointes. This $Ca^{2+}$-independent activity is enhanced by long stimulating pulses (De Koninck and Schulman (1998) *Science* 279:227–230), as occur with prolonged action potential repolarization. It is possible that EADs caused by $I_{Ca}$ may be enhanced by increased $[Ca^{2+}]_i$ through the CaM kinase II pathway. However, not all EADs are due to $I_{Ca}$, and EADs can occur in conditions adverse to CaM kinase activity such as enhanced $[Ca^{2+}]_i$ buffering.

Delayed afterdepolarizations (DADs) are another cause of ventricular arrhythmias associated with intracellular calcium overload. DADs are caused by an inward current that follows completion of action potential repolarization. This inward current is a marker of intracellular calcium overload (Thandroyen et al. (1991) *Circ Res* 69:810–819). Intracellular calcium overload is a central feature of many ventricular arrhythmias occurring during ischemia (Lee et al. (1988) *Circ* 78:1047–1059) including ventricular fibrillation.

Inhibition of CaM kinase activity can be used to test for a facilitatory role of CaM kinase in EADs and DADs. There are several methods for blocking CaM kinase activity. Synthetic pseudo-substrate peptide inhibitors of CaM kinase provide a specific approach to CaM kinase inhibition and have been used in a variety of cell types including ventricular myocytes (Braun et al. (1995) *J. Physiol* 488:37–55). The peptide sequence KKALHRQEAVDCL (SEQ ID NO:1), like other similar peptides, was found to inhibit CaM kinase in a highly specific manner. SEQ ID NO:1 is a much less efficient inhibitor of both protein kinase A (PKA) and protein kinase C (PKC), with an $IC_{50}$ value of at least 500 $\mu$mol/l for each. Myristoylated inhibitory peptides are cell membrane permeant and thus could also be effective when added extracellularly.

A variety of cell—membrane permeant organic CaM kinase and calmodulin inhibitors are available and widely used (Braun et al. (1995) *Ann Rev Physiol* 57:417–445). A principle disadvantage for these inhibitors as experimental agents is that many of them directly block $I_{Ca}$.

However, direct $I_{Ca}$ blockade by the CaM, kinase inhibitor KN-93 has not been previously reported. KN-93 (2-[N-(2-hydroxyethyl)-N-(4-methoxy-benzenesulfonyl)]-amino-N-(4-chlorocinnamyl)-N-methylbenzylamine) is a methoxybenzene sulfonamide derivative that competitively inhibits calmodulin binding to CaM kinase with a reported $K_i$ of 0.37 $\mu$mol/l. KN-93 has been shown to inhibit CaM kinase—dependent processes in PC12h cells, fibroblasts, and gastric parietal cells. There are four isoform groups of CaM kinase II ($\alpha,\beta,\gamma,\delta$) and the $\delta_B$ and $\delta_C$ isoforms have been identified in myocardium. The catalytic and regulatory domains in CaM kinase are highly conserved in all known CaM kinase isoforms so inhibitors that interact with either of these domains are expected to work in all cell types including cardiac. KN-92 (2-N-(4-methoxybenzenesulfonyl)-amino-N-(4-chlorocinnamyl)-N-methylbenzylamine) is a congener of KN-93 without CaM kinase inhibitory activity and is used as an experimental control. Direct $I_{Ca}$ blockade by KN-92 has also not been previously reported, and neither KN-93 nor KN-92 have appreciable effects on other serine threonine kinases such as protein kinase A (PKA) or protein kinase C (PKC).

Two general approaches are currently used to suppress ventricular arrhythmias due to action potential prolongation, in addition to ICD implantation. One is to shorten the action potential using antiarrhythmic agents (e.g. mexilitine, pinacidil) or by increasing the heart rate using artificial pacing or the β-adrenergic agent isoproterenol. The second is to indirectly suppress protein kinase A (PKA), which enhances L-type calcium current and calcium release from the sarcoplasmic reticulum, through left stellate ganglionectomy or with β-adrenergic blocking drugs. Neither of these approaches is broadly applicable for two reasons: 1) action potential duration is governed by a number of different ionic currents and it is not typically known which current is critical in a given patient. Furthermore, specific antiarrhythmic drugs are not available for modification of many of these ionic currents. In addition, not all causes of action potential prolongation respond to pacing by action potential shortening. Isoproterenol also does not always shorten the action potential, can itself be arrhythmogenic, may cause ischemia, and can only be used in an acute setting. 2) At present, suppression of PKA is accomplished indirectly by stellate gangionectomy or by β-adrenergic antagonists. β-adrenergic antagonists are effective in reducing death from arrhythmias, but application is limited by the fact that these agents weaken the force of heart muscle contraction.

Ventricular arrhythmias due to ischemia and intracellular calcium overload are generally treated with revascularization (i.e. coronary artery angioplasty or coronary artery bypass surgery), β-adrenergic antagonists, and class III antiarrhythmic medications (e.g. sotalol and amiodarone), in addition to ICDs. Unfortunately revascularization is often incomplete and the recurrence rate of ventricular fibrillation is significant. Class III antiarrhythmic agents may be proarrhythmic by causing excessive action potential prolongation or be associated with use—limiting toxicity (e.g. amiodarone). Beta-adrenergic antagonist use is also limited as previously discussed (above).

Atrial fibrillation is associated with significant morbidity and mortality from stroke and heart failure. Atrial fibrillation can be caused by DADs. Maintenance of atrial fibrillation is favored by intracellular calcium dependent processes. (Tieleman et al. (1997) Circ 95:1945–1953) Present conventional therapies center around anticoagulation (for prevention of stroke), ventricular rate control, and antiarrhythmic agents. Currently available antiarrhythmic agents only succeed in maintaining sinus rhythm in ~50% of patients/year. Recent experimental therapies include artificial pacing systems and atrial ICDs.

CaM kinase inhibition may be superior to previous antiarrhythmic strategies because CaM kinase has characteristics that may allow it to function as a proarrhythmic positive feedback effector for EADs and DADs, and thus play a more central role in EAD and DAD induction than other effectors, such as PKA. L-type calcium current increases intracellular calcium directly by transmembrane calcium flux and indirectly through calcium-induced release of calcium from the sarcoplasmic reticulum. Increased intracellular calcium results in enhanced CaM kinase activity to further favor EADs during action potential prolongation. In contrast, PKA activity is not enhanced by increased intracellular calcium. Direct CaM kinase inhibitors are available (above) and CaM kinase inhibition does not reduce the strength of contraction in isolated hearts, suggesting it may be applicable in patients who do not tolerate β-adrenergic antagonists. Recent experiments using genetically engineered mice lacking neuronal CaM kinase isoforms suggest that systemic CaM kinase inhibition will not result in intolerable side effects. It is likely that redundant CaM kinase isoforms or other signal transduction mechanisms partially compensate for the inactivity of one CaM kinase subtype, so the actual effects of knockout or other inhibition strategies are less deleterious than anticipated. Thus, CaM kinase inhibition may be highly beneficial as a treatment for arrhythmias related to excessive action potential prolongation and EADs and for arrhythmias related to intracellular calcium overload such as atrial and ventricular fibrillation.

Action potential prolongation favors increased L-type calcium current, and this current is the likely proximate cause of the arrhythmias, but because calcium is essential for cardiac muscle function, direct blockade of L-type calcium current is not a viable antiarrhythmic strategy. L-type $Ca^{2+}$ current inhibitors have not been found to be highly effective antiarrhythmic agents for atrial and ventricular fibrillation as well as most types of ventricular tachycardia. Lack of ventricular antiarrhythmic efficacy for $I_{Ca}$ antagonists at clinically tolerated doses may be because the amount of $I_{Ca}$ inhibition is insufficient to prevent or terminate most EADs. Combination of a $I_{Ca}$ antagonist with a CaM kinase inhibitor may be effective, however.

SUMMARY OF THE INVENTION

The present invention provides methods for treating and preventing arrhythmias in a human subject through the administration of a multifunctional calcium/calmodulin-dependent protein kinase inhibitor to the human in an amount sufficient to suppress early after depolarizations, delayed afterdepolarizations, or intracellular calcium overload.

Also provided are pharmaceutical compositions comprising a multifunctional calcium/calmodulin-dependent protein kinase inhibitor and a pharmaceutically acceptable excipient.

Another aspect of the invention provides for methods of identifying agents useful in the treatment of arrhythmias and provides feasible strategies for the development of a therapeutic, antiarrhythmic drug which can be applied systemically.

In another embodiment, the present invention provides for, methods of treating and preventing arrhythmias in which a multifunctional calcium/calmodulin-dependent protein kinase inhibitor is administered in combination with a second antiarrhythmic agent in order to increase safety and efficacy of the treatment.

In another embodiment, the present invention provides for methods of treating and preventing arrhythmias in which the administration of a multifunctional calcium/calmodulin-dependent protein kinase inhibitoris is combined with treatment of the patient with an antiarrhythmic device.

The present invention also provides for the administration of a multifunctional calcium/calmodulin-dependent protein kinase inhibitor in combination with a second antiarrhythmic agent to block the proarrhythmic effects due to action potential prolongation caused by the second antiarrhythmic agent.

DESCRIPTION OF THE FIGURES

FIG. 1. (A) Experimental design for early afterdepolarizations (EAD) induced by clofilium in an isolated rabbit heart pretreated with, the inactive analog, KN-92. Data tracings show (from top to bottom) moniophasic action potentials (MAP) and left ventricular (LV) pressure. The horizontal lines to the left of the, LV pressure tracings (top to bottom) indicate 100 mm Hg and 0 mm Hg levels and 850 ms for panels A and B. All experiments with isolated hearts consisted of 3 periods. A fourth period (experimental period 4) was only added in hearts with EADs. Experimental periods are labeled 1–4 (top of page for both panels A and B). Experimental period 1 measurements represent control and follow >10 min of stabilization. Experimental period 2 measurements are taken 10 min after addition of the inactive KN-93 analog, KN-92 (0.5 $\mu$mole/l). Period 3 measurements follow addition of clofilium (7.5 $\mu$mole/l) and are taken at EAD initiation or from the longest action potential duration recorded over 30 min. Multiple EADs are seen as 2 oscillations during repolarization on the MAP tracings in experimental period 3. Secondary elevations in LV pressure coinciding with EADs are also seen in the LV pressure tracing in experimental period 3. Experimental period 4 measurements follow EAD termination by addition of nifedipine (10 $\mu$mole/l) (shown above) or $Cd^{2+}$ (200–500 $\mu$mole/l) (data not shown). The horizontal bars indicate the experimental conditions for both panels A and B. (B) Experimental design for isolated rabbit hearts treated with CaM kinase inhibitor KN-93. Arrangement of data tracings is the same as in FIG. 1A (above). Experimental periods are also the same as in FIG. 1A (above) except the active CaM kinase inhibitor KN-93 (0.5 $\mu$mole/l) was added 10 min prior to period 2 measurements. Period 4 was omitted because EADs did not appear within 30 min after addition of clofilium. (C) Continuous record of EAD termination by nifedipine (10 $\mu$M) in a heart paced at a cycle length of 1500 ms. Data tracings show MAP with single EADs (top) and LV pressure (bottom). The horizontal lines to the left of the LV pressure tracings indicate 50 mm Hg and 0 mm Hg pressure levels (top to bottom). EAD termination occurs prior to the first discernible decrease (i.e. >10% below baseline) in LV pressure. The vertical arrow marks the first beat of EAD termination.

FIG. 2. Left ventricular developed pressure (LVDP, panel A) and interbeat intervals (panel B) in isolated rabbit hearts. LVDP is defined as the peak systolic pressure minus the end diastolic pressure. Numerals 1–4 correspond to the experimental periods illustrated in FIGS. 1A and B. The data set shown in panels A and B is clofilium (7.5 $\mu$mole/l, n=21); the CaM kinase inhibitor KN-93 (0.5 $\mu$mole/l, n=10, open circles) or the inactive analog KN-92 (0.5 $\mu$mole/l, n=11, filled circles); EAD termination, nifedipine (10 $\mu$mole/l, n=7) or $Cd^{2+}$ (200–500 $\mu$mole/l, n=4). Experimental period 4 only includes data from hearts demonstrating EADs; in this last group, n=11 because 3 MAP recordings were lost upon EAD termination. LVDP at experimental period 4 is taken from the first beat after EAD termination as shown in FIG. 1C. A. Hearts pre-treated with KN-93 failed to increase LVDP following clofilium treatment (panel A, experimental period 3). LVDP did increase significantly after clofilium addition in hearts treated with the inactive analog KN-92: *p=0.014 compared with period 1; p=0.002 compared with KN-92 treated hearts in period 3. B. Interbeat intervals increased compared with control period intervals both in hearts treated with KN-93 (p=0.02) and in hearts treated with the inactive analog KN-92 (*p=0.049). No significant differences in interbeat intervals were present between hearts treated with the CaM kinase inhibitor KN-93 or the inactive analog KN-92.

FIG. 3. Monophasic action potential durations (MAP) at 50% ($APD_{50}$, circles) and 90% ($APD_{90}$, squares) repolarization to baseline in isolated rabbit hearts. Numerals 1–4 correspond to the experimental periods illustrated in FIGS. 1A and B. Filled symbols are for hearts pretreated with the inactive analog KN-92. Open symbols are for hearts pretreated with the CaM kinase inhibitor KN-93. The data set is the same as in FIG. 2. *p=0.004 and **p<0.001 compared with corresponding APDs in period 1. No significant differences in MAP durations were present between hearts pretreated with the CaM kinase inhibitor KN-93 or the inactive analog KN-92. MAP durations were not significantly different during early afterdepolarizations (EAD) and the first beat after EAD termination by nifedipine (10 $\mu$mole/l) or $Cd^{2+}$ (200–500 $\mu$mole/l).

FIG. 4. Percent calcium-independent CaM kinase activity in isolated rabbit hearts. Maximal (i.e. $Ca^{2+}$/calmodulin-dependent) and $Ca^{2+}$-independent CaM kinase activities were assayed from left ventricular (LV) tissue homogenates as described in Example 5, Experimental Methods. All hearts were initially isolated under control conditions. A stabilization period of $\geq$10 min was used for each isolated heart to ensure the absence of EADs, as indicated by monophasic action potentials (MAPs) recorded by a catheter positioned over the LV epicardium. To assay for CaM kinase activity, a left ventricular epicardial slice (1–2 g tissue) was cut from hearts in each of the three groups as follows: 1) Control (n=5), slice removed after $\geq$10 min stabilization period; 2) Clofilium (n=5), slice removed after addition of 7.5 $\mu$mole/l clofilium and $\geq$10 min of EADS as verified by MAP recordings; 3) KN-93, Clofilium (n=6), slice removed $\geq$10 min after addition of 7.5 $\mu$mole/l clofilium in hearts pretreated with 0.5 $\mu$mole/l KN-93. *p=0.015 compared to both the Control group and the KN-93, Clofilium group.

FIG. 5. Effects of KN-93 and KN-92 on CaM kinase activity in vitro. CaM kinase activity in left ventricular tissue homogenate was assayed as described in Example 5, Experimental Methods. The plot shows that increasing concentrations of KN-93, but not the inactive analog KN-92, produce direct inhibition of cardiac CaM kinase activity. The solid line represents a fit to the KN-93 data using the Hill equation. The dashed line shows the expected inhibition of CaM kinase activity after accounting for the concentration of added calmodulin in the assay (150 $\mu$mole/l), given the competitive interaction between KN-93 and calmodulin with CaM kinase.(Sumi et al. (1991) *Biochem Biophys Res commun* 181: 968–975) The $K_i$ value for inhibition by KN-93 calculated from the dashed curve is 2.58 $\mu$mole/l.

FIG. 6. KN-93 and KN-92 effects on L-type $Ca^{2+}$ current ($I_{Ca}$). (A). Peak steady state current voltage (I–V) relationship for $I_{Ca}$ during control conditions (filled squares) and following addition of the inactive agent KN-92 (0.5 $\mu$mol/l filled circles and 1.0 $\mu$mol/l filled diamonds) to the cell bath. The inset shows superimposed raw currents and the command voltage step (300 ms) from the ventricular myocyte used to construct the I–V relationship. The horizontal bar marks the zero current level. (B). Tracings are laid out as in A. (above) except the CaM kinase inhibitor KN-93 was added to the cell bath (0.5 $\mu$mol/l open circles and 1.0 $\mu$mol/l open diamonds). (C). Dose response relationships for peak steady state $I_{Ca}$, recorded during command voltage steps from a holding potential of –80 mV to a test potential of 0 mV, and the CaM kinase inhibitor KN-93 (open circles) or the inactive analog KN-92 (filled circles). Data are expressed as a fraction of control $I_{Ca}$. The total number of.cells studied during each plotted measurement is given in parentheses. KN-93 and KN-92 were equipotent peak steady state $I_{Ca}$ inhibitors at the concentration used to suppress early afterdepoloarizations in this study, but KN-93 was a more effective $I_{Ca}$ inhibitor at 1.0 $\mu$mol/l. (D). Time dependence of $I_{Ca}$ recovery from inactivation. Peak $I_{Ca}$ was elicited from a holding potential of –80 mV to atest potential of 0 mV for 300 ms (P1). Progressively longer intervals (10–2500 ms) were inserted between P1 and a second pulse (P2). Peak $I_{Ca}$ during P2 was expressed as a fraction of peak $I_{Ca}$ during P1. Data are plotted for control conditions (filled squares) in the presence of 0.5 $\mu$mol/l KN-92 (filled circles) or 0.5 $\mu$mol/l KN-93 (open circles).

FIG. 7. CaM kinase inhibition suppresses pacing induced inward current. Isolated heart cells were paced (0.5 Hz, T=32° C.) using a prolonged action potential voltage clamp command wave form. (A) A prolonged action potential was digitized and used as a voltage clamp command waveform for current tracings below. Command membrane potential is on the ordinate and time (for panels A–C) is on the abscissa (B) Inward currents developed after completion of the command wave form in 5/6 cells dialyzed with a control peptide (SEQ ID NO:2, 20 μmole/l) devoid of CaM kinase inhibitory activity. Cell membrane currents are referenced on the ordinate for both panels B and C. (C) Inward currents did not develop in any (0/5) cells dialyzed with the active CaM kinase inhibitory peptide (SEQ ID NO:1, 20 μmole/l). In addition, ryanodine (10 μmole/l), a blocker of intracellular calcium release, also prevented inward current development in 2/2 cells tested.

DETAILED DESCRIPTION OF THE INVENTION

We have discovered a method for treating arrhythmias in which a multifunctional calcium/calmodulin-dependent protein kinase inhibitor is administered to the patient in an amount sufficient to suppress early afterdepolarizations, delayed afterdepolarizations, or intracellular calcium overload. The present invention also provides for the prevention of the occurrence of arrhythmias through the administration of a multifunctional calcium/calmodulin-dependent protein kinase inhibitor to the patient patient in an amount sufficient to suppress early afterdepolarizations, delayed afterdepolarizations, or intracellular calcium overload.

The term "CaM kinase" is used herein to refer to any member of the multifunctional calcium/calmodulin-dependent protein kinase family in general, whereas the term "CaM kinase II" is used herein only to refer to the multifunctional calcium/calmodulin-dependent protein kinase II (and its isoforms).

An "inhibitor" of CaM kinase is a compound capable of decreasing the activity of the enzyme (generally via noncovalent binding of the inhibitor to the enzyme). The inhibitor may provide reversible inhibition. Reversible inhibition can consist of competitive inhibition, noncompetitive inhibition, uncompetitive inhibition, or mixed inhibition. An "inhibitor" of CaM kinase can also be an irreversible inhibitor or it can be a suicide inhibitor.

In a preferred embodiment of the invention, an inhibitor of a multifunctional calcium/calmodulin-dependent protein kinase II is used in the treatment and prevention of arrhythmias. However, the use of compounds which inhibit other members of the family of multifunctional calcium/calmodulin-dependent protein kinases is also provided for by the present invention. The family of multifunctional calcium/calmodulin-dependent protein kinases includes CaM kinase I, CaM kinase II, and CaM kinase IV. Each of these members also additionally exists in a multitude of isoforms. An inhibitor of one of the multifunctional calcium/calmodulin-dependent protein kinases is generally understood by one skilled in the art to be likely to inhibit the other members of the family as well, due to structural conservation amongst the types (Enslen et al. (1994) *J. Biol. Chem.* 269:15520–15527).

In another embodiment of the present invention, isoform-specific inhibitors could be used as agents with enhanced specificity in the prevention and treatment of arrhythmias (Braun et al. (1995) *J. Physiol* 488:37–55). In still another embodiment, organ-specific CaM kinase inhibtors could be used. Cardiac specificity of a multifunctional calcium/calmodulin-dependent protein kinase may be achieved by combining a CaM kinase inhibitor with cardiac cell specific epitope recognition sequences. The use of organ or isoform specific inhibitors may help ensure efficacy and the safety of systemic delivery of the drug.

Existing CaM kinase inhibitors such as KN-93 and any of the inhibitory peptides such as KKALHRQEAVDCL (SEQ ID NO:1) can be used in the methods of treating arrhythmias described herein. Both inhibitors act competitively, but at distinct sites on the kinase. KN-93 binds and prevent activation by calmodulin, whereas SEQ ID NO:1 binds to the catalytic site, preventing interaction with substrate molecules. Other general, organ-specific, or isoform-specific CaM kinase inhibitors may also be used in the treatment of arrhythmia as provided for by the present invention.

Administration of the inhibitor to the patient may be accomplished through any one of a variety of methods known to those skilled in the art. In a preferred embodiment, the inhibitor is delivered systemically. In a further preferred embodiment, the CaM kinase inhibitor is delivered intravenously. Other possible methods of delivery include, but are not limited to oral delivery, bolus injection or continuous parenteral pump infusion, cutaneous patch or cutaneous iontophoretic delivery, and intracoronary or intrapericardial delivery, or gene transfer therapy, as recently described by Griffith et al. (Griffith et al. (1993) *Neuron* 10:501–509).

An "arrhythmia" is a disturbance in the heart's natural rhythm. According to the present invention, the arrhythmia may be any atrial or ventricular arrhythmia associated with a prolonged action potential, early afterdepolarizations, delayed afterdepolarizations, or intracellular calcium overload. Cardiac conditions which involve such arrhythmias include, but are not limited to, long QT syndrome, cardiomyopathy, and the proarrhythmic effects of certain medications including antiarrhythmic drugs and ischemia. Other structural abnormalities of the heart, abnormalities of the heart's electrical system, and diseases may also cause arrhythmias treatable by the present invention. One particular clinical indication for intervention is the presence of prolonged QT intervals (>480 ms). The arrhythmia to be treated may be life-threatening. A preferred embodiment of the present invention is the treatment of ventricular tachycardia, an arrhythmia associated with early afterdepolarizations. Treatment of atrial and ventricular fibrillation, arrhythmias associated with DADs and intracellular overload are also provided for by the invention.

A "sufficient amount" or an "effective amount" of a multifunctional calcium/calmodulin-dependent protein kinase inhibitor according to this invention is an amount sufficient to suppress early afterdepolarizations (EADs), delayed afterdepolarizations (DADs), or intracellular calcium overload. Early afterdepolarizations are depolarizing oscillations in the action potential and their likelihood of occurrence is increased by the prolongation of action potential repolarization. They are also a probable cause of some lethal arrhythmias. Delayed afterdepolarizations are a marker of intracellular calcium overload and also the cause of some lethal arrhythmias.

An effective amount of inhibitor will vary with the activity of the inhibitor. In one embodiment of the invention, from about 0.05 to about 5.0 mg of inhibitor per kilogram of subject's body weight is administered. In a preferred embodiment, from about 0.3 to about 3.0 mg per kilogram is administered. In another embodiment, this dosage could be repeated every thirty to sixty minutes until suppression of early afterdepolarizations is achieved, unless limited by the development of hypotension due to the Ca channel blocking effect. In another embodiment, a myristoylated CaM kinase inhbitory peptide is administered at a dose of from about 2 to about 20 µmole per kilogram of body weight.

In one embodiment, the administration of a CaM kinase inhbitor may also be combined with administration of a second antiarrhythmic agent to the patient. This combination may provide benefits both in terms of efficacy and safety. In a preferred embodiment, the CaM kinase inhibitor is administered to the patient in conjunction with a second antiarrhythmic agent that is known to have a proarrhythmic effect. Existing antiarrhythmic agents which may be delivered to a patient in combination with the CaM kinase inhibitor include K-channel blockers, such as the class IA or III antiarrhythmic drugs. In one embodiment of the invention, the class IA agents procainamide (1.0 gram i.v. loading dose followed by 1–3 mg/min i.v.) or quinidine (~70 mg/Kg/24 hours) would be administered with a CaM kinase inhibitor. In another embodiment of the invention, the class III agents dofetilide (8 µg/Kg i.v.) or d-sotalol (5.7 mg/Kg/24 hours p.o.) would be administered with a CaM kinase inhibitor.

In another embodiment, the administration of a CaM kinase inhibitor may also be combined with administration of a β-adrenergic antagonist to increase efficacy of antiarrhythmic therapy. In one embodiment of the invention, the β-adrenergic antagonist atenolol (50–100 mg/day p.o./i.v.), propranalol (60 mg/6 hours p.o. or 30 mg/6 hours i.v.), or metoprolol (50–100 mg/6 hours p.o./i.v.) would be administered with a CaM kinase inhibitor.

In another embodiment, the administration of a CaM kinase inhibitor may also be combined with administration of a calcium channel blocker to increase efficacy of antiarrhythmic therapy. In one embodiment of the invention, the calcium channel antagonist nifedipine (10–30 mg/6 hours p.o.), verapamil (80–120 mg/6 hours p.o. or 0.075–0.15 mg/Kg i.v.), diltiazem (30–90 mg/6 hours p.o. or 0.075–0.15 mg/Kg i.v.), mibefradil (50–100 mg/day p.o.) would be administered with a CaM kinase inhibitor.

In another embodiment of the invention, the administration of a CaM kinase inhibitor may be combined with a treatment that utilizes an antiarrhythmic device. This combination is useful in treating and preventing arrhythmias. In a preferred embodiment, the antiarrhythmic device is an implantable cardiac defibrillator (also referred to herein as an implantable cardioverter defibrillator). For instance, the administration of a CaM kinase inhibitor may be combined with an implantable atrial cardiodefibrillator to treat atrial fibrillation. In another embodiment, the administration of a CaM kinase inhibitor may be combined with an implantable ventricular cardiodefibrillator to treat ventricular fibrillation. In still another embodiment, the administration of a CaM kinase inhibitor may be combined with a permanent pacing system to prevent atrial fibrillation.

In another embodiment, the present invention provides for a pharmaceutical composition of a calcium/calmodulin-dependent protein kinase inhibitor and a pharmaceutically acceptable excipient. In a preferred composition, an inhibitor of CaM kinase II is used.

A "pharmaceutically acceptable excipient" or "carrier" is a therapeutically inert substance which serves as a diluent or delivery vehicle for the inhibitor drug. Selection of suitable carriers for the pharmaceutical composition is readily achievable by one skilled in the art and would in part be dictated by the specific CaM kinase inhibitor chosen. Typical pharmaceutical compositions useful for CaM kinase II inhibitors are disclosed in Remington, *The Science and Practice of Pharmacy*, 19th ed., 1995, Mack Publishing Co., Easton, Pa., the disclosure of which is incorporated by reference herein. Possible pharmaceutical excipients include polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

A method for identifying agents useful in the treatment or prevention of arrhythmias is also provided by the present invention. Screening for novel antiarrhythmia agents may be conducted by determining if the agent inhibits CaM kinase II activity. One test for CaM kinase II inhibition is described herein; however, alternative methodologies for identifying inhibitors via exposure to CaM kinase II are within the purview of this invention. The test for CaM kinase II inhibition may be done in vivo, but is preferably done in vitro. The ability of an assayed compound to inhibit the activity of CaM kinase II to an appreciable degree indicates that the compound will have antiarrhythmic properties.

The invention also provides for methods of suppressing early and delayed afterdepolarizations and intracellular calcium overload in a mammal. This suppression is achieved by the administration of an inhibitor of a multifunctional calcium/calmodulin-dependent protein kinase to the subject. In a preferred embodiment, the inhibitor is a CaM kinase II inhibitor.

Another aspect of the invention provides for methods of treating arrhythmia in a human by decreasing the activity of a CaM kinase in the human. This decrease in activity may be achieved through a number of ways, each readily discernible by one skilled in the art. In one embodiment, the activity of CaM kinase is decreased by the administration of a CaM kinase inhibitor to the subject. In other embodiments, the activity of a CaM kinase may be achieved through other means such as by decreasing the level of expression of a CaM kinase in a human by an antisense strategy or similar method.

The present invention, in all aspects, is enabled by our discovery that EADs and DADs are due to $I_{Ca}$ and/or intracellular calcium overload and are facilitated by a multifunctional calcium/calmodulin-dependent protein kinase.

Figure 2:
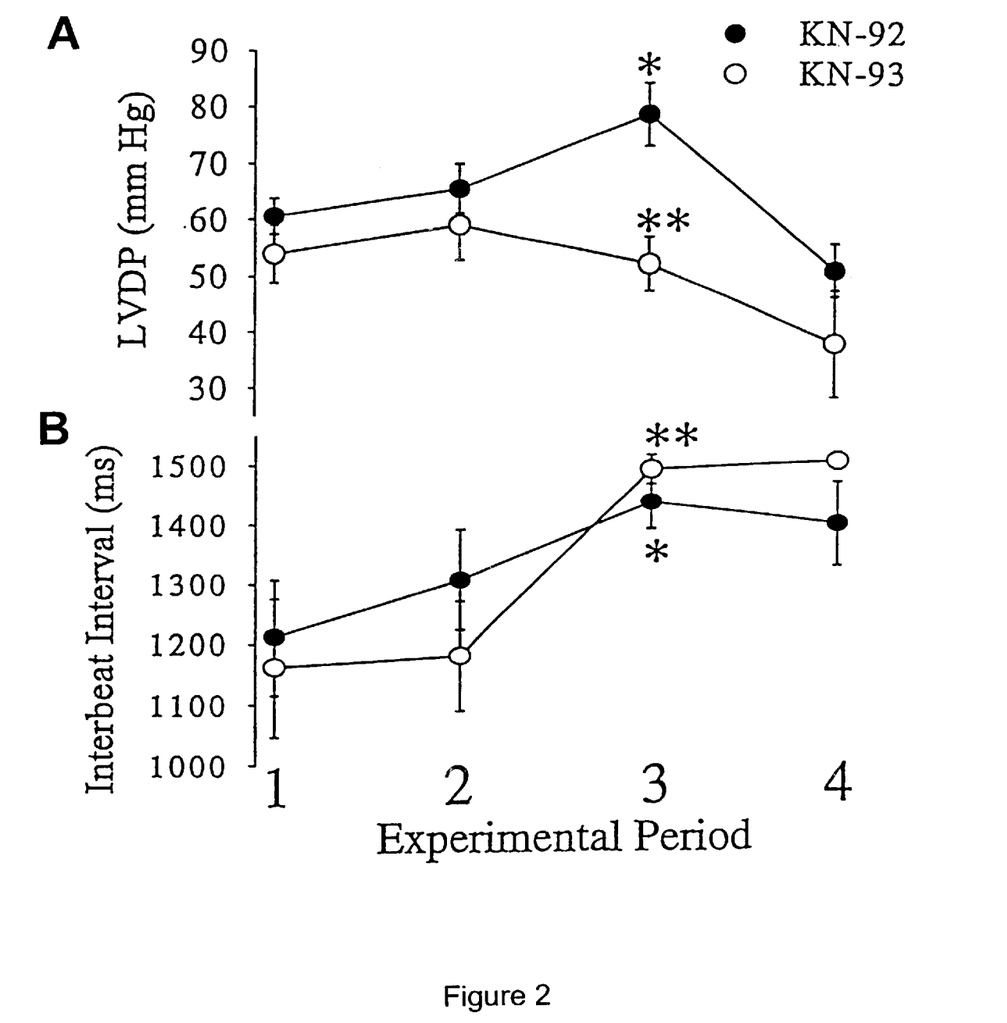
Figure 3:
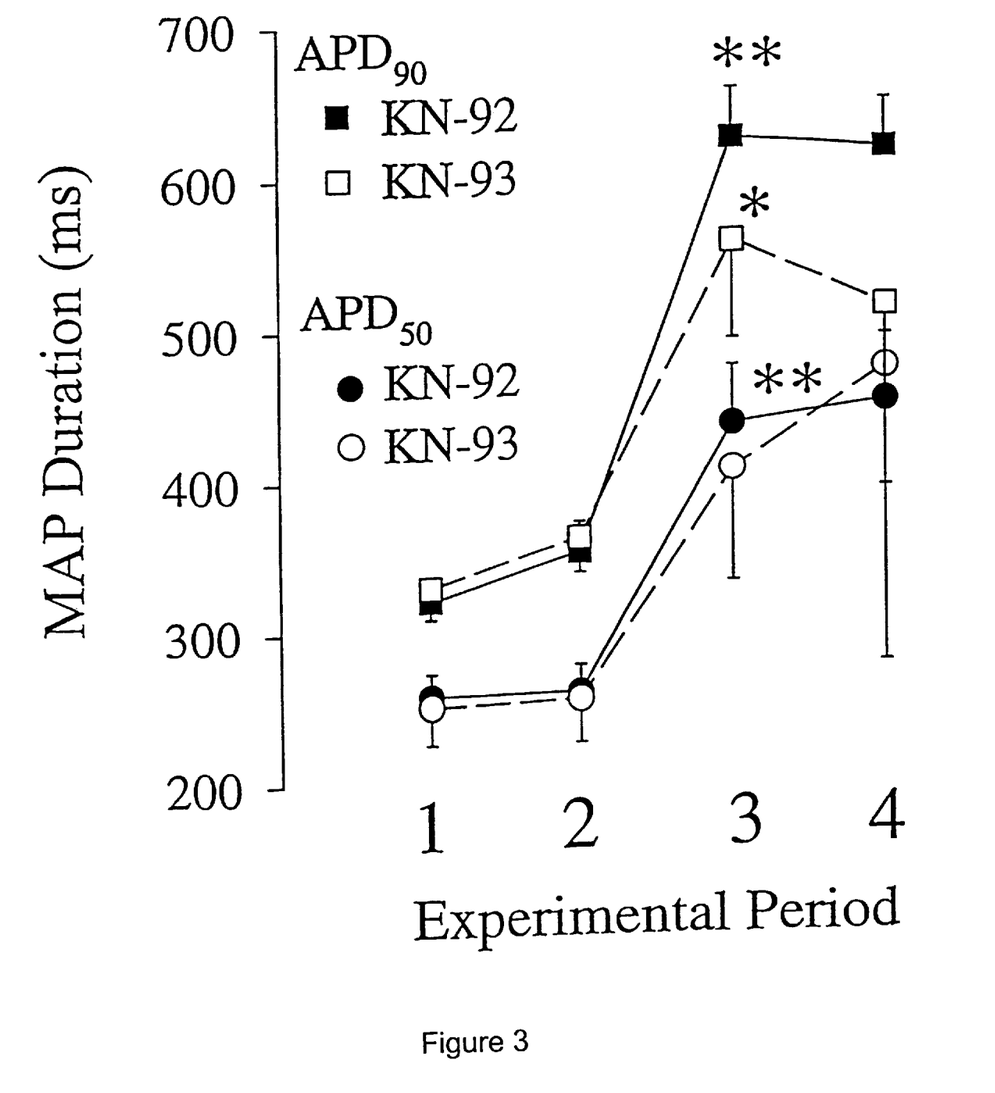

In our experiments, EADs were monitored with monophasic action potential (MAP) catheters. Reliable EAD induction was achieved using hypokalemia, bradycardia, and the Vaughn-Williams class III antiarrhythmic agent clofilium in isolated perfused rabbit hearts. We first showed a role for $I_{Ca}$ in clofilium-induced EADs using the specific $I_{Ca}$ antagonists nifedipine and $Cd^{2+}$ (Example 1). EAD termination by $I_{Ca}$ antagonists appeared to be a direct effect of $I_{Ca}$ blockade, and not a secondary effect of $[Ca^{2+}]_i$ depletion, because of its 1) rapid onset (FIG. 1) and 2) occurance before significant loss of LVDP (FIG. 2). The lack of MAP shortening at EAD termination is further evidence that EAD termination is a direct effect of $I_{Ca}$ blockade and not due to a secondary effect on MAP duration (FIG. 3).

Further studies in isolated rabbit hearts examined the role of CaM kinase in facilitating EADs using the active CaM kinase inhibitor KN-93. Parallel experiments with the inactive analog KN-92 served as controls (Examples 2 and 3, FIGS. 1–3). Our experiments showed that the CaM kinase inhibitory drug KN-93, but not its inactive analog, KN-92, significantly decreased the inducibility of EADs in the whole heart model independent of other factors known to promote EADs. Action potential duration was not different in hearts pretreated with KN-92 or KN-93 before or after clofilium (FIG. 3). Similarly, heart rates in the KN-92 and KN-93 pretreated hearts were not different (FIG. 2). Whole cell mode voltage clamp experiments with isolated rabbit ventricular myocytes established that KN-93 and KN-92 are equipotent direct blockers of $I_{Ca}$ at the concentration (0.5 µmol/l) used in the isolated heart experiment (Example 6, FIG. 6). However, ventricular CaM kinase activity was significantly inhibited by KN-93 ($K_i \leq 2.58$ µmol/l), but not by KN-92, based on the results of an in vitro assay (Example 5, FIG. 5).

Corroborating results were obtained with a second CaM kinase inhibitor, a highly specific pseudo-substrate peptide, and an appropriate control (Example 7). The specificity of the peptides used excludes the possibility of PKA and PKC being important mediators of arrhythmogenic calcium current during these EADs.

The clofilium-induced increase in action potential duration is expected to increase $Ca^{2+}$ entry via $I_{Ca}$. In addition to mediating $Ca^{2+}$ enhancement of $I_{Ca}$, CaM kinase interacts with other $[Ca^{2+}]_i$ dependent processes in ventricular myocytes. CaM kinase both facilitates $Ca^{2+}$ uptake by the sarcoplasmic reticulum and release by the ryanodine receptor. The anticipated net effect of CaM kinase activation in ventricular myocytes is increased LVDP. Clofilium did increase LVDP in KN-92 but not KN-93 pretreated hearts (FIG. 2). Once activated by $[Ca^{2+}]_i$, CaM kinase II undergoes intersubunit autophosphorylation which results in $Ca^{2+}$-independent CaM kinase II activity. Measurement of $Ca^{2+}$-independent activity by CaM kinase, thus, provides an important measure of CaM kinase activation. We found that $Ca^{2+}$-independent activity is significantly increased during EADs and this increase is prevented by pretreatment with the CaM kinase inhibitor KN-93 (Example 4, FIG. 4) at the same concentration found to suppress EADs.

Figure 7:
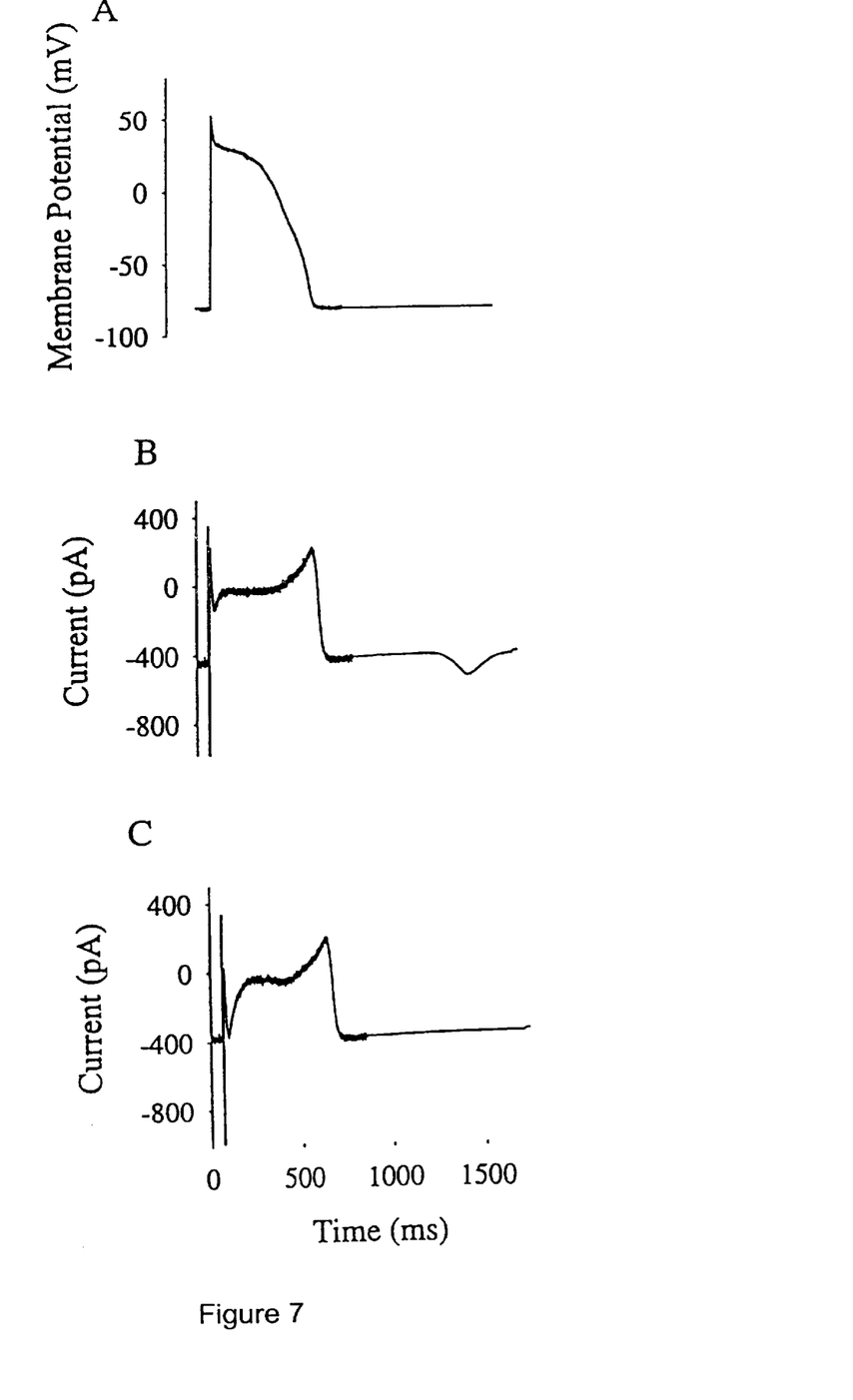

In an additional set of experiments we applied repetitive stimulation of isolated heart cells using voltage clamp with a prolonged action potential wave form (Example 8, FIG. 7). Inward currents consistently developed in cells treated with an inactive control peptide (FIG. 7B). These inward currents underlie: delayed afterdepolarizations and are known to result from intracellular calcium overload (Thandroyen et al. (1991) Circ Res 69:810–819). Inward currents were prevented in all cells treated with a specific CaM kinase inhibitory peptide (Example 8, FIG. 7C). Ryanodine, an agent that prevents intracellular calcium overload by blocking release of calcium from intracellular stores, also prevented development of the inward current in a separate group of cells. Thus, CaM kinase inhibition is effective in preventing inward currents known to both report intracellular calcium overload and underlie DADs.

These results support the hypothesis that CaM kinase is activated during EADs. The findings that 1) CaM kinase inhibition reduces EAD inducibility and 2) EADs and MAP duration prolongation increase CaM kinase activity together suggest that CaM kinase is a proarrhythmic positive feedback effector for EADs. CaM kinase inhibition also suppressed inward currents associated with DADs and intracellular calcium overload. Therefore, we have established CaM kinase to be a novel antiarrhythmic drug target.

The following specific examples are intended to illustrate the invention and should not be construed as limiting the scope of the claims.

EXAMPLES

Example 1

Figure 1:
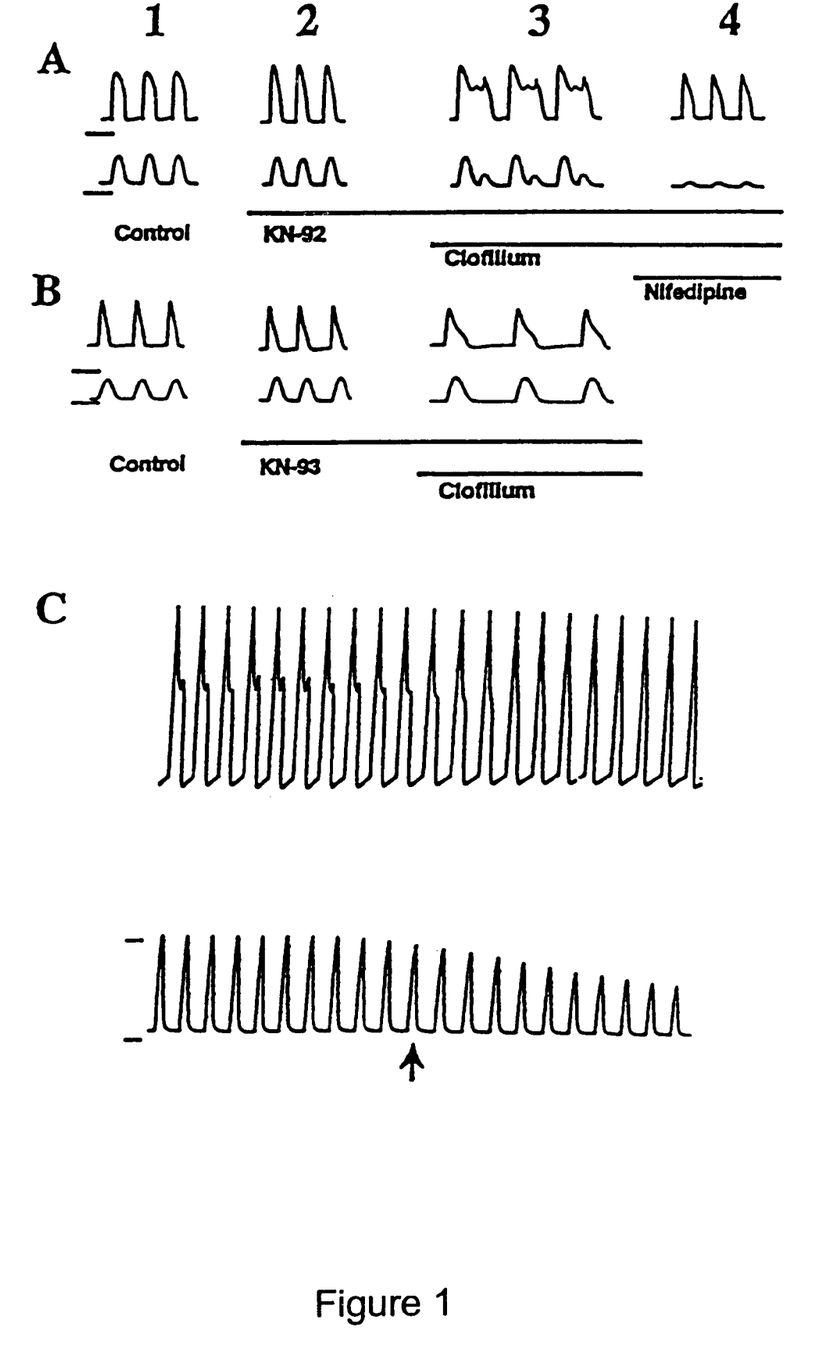

Clofilium-Induced Early Afterdepolarizations are Terminated by L-Type $Ca^{2+}$ Current Antagonists The experimental design for the isolated heart experiments is shown in FIG. 1A. All clofilium-induced EADs were terminated by the $I_{Ca}$ antagonists $Cd^{2+}$ (200–500 µmol/l) or nifedipine (10 µmol/l). EAD termination occurred in <10 sec from a discernable decrease (>10% from preceeding baseline) in LVDP after addition of $I_{Ca}$ antagonist to the perfusate. EAD termination occurred before LVDP decreased significantly (FIG. 2A) and without a change in the interbeat interval (FIG. 2B). Action potential duration was not shortened upon the first beat of EAD termination. EAD termination by $I_{Ca}$ antagonists was unlikely due to a secondary effect on $[Ca^{2+}]_i$ because LVDP was not significantly depressed at initial termination. EAD termination by $I_{Ca}$ antagonists was not due to secondary effect on MAP duration or heart rate. These results support the hypothesis that clofilium-induced EADs are directly due to $I_{Ca}$.

Experimental Methods

New Zealand White rabbits of either gender (2.7–3.2 kg) were treated with a heparin bolus (150 U/kg IV) and killed by pentobarbital (50 mg/kg IV) overdose. Hearts were rapidly excised and placed in ice-cold Tyrode's solution for dissection of extracardiac tissue. (Tyrode's solution was composed of (mmol/l) NaCl (130.0), $NaHCO_3$ (20.0), glucose (5.6), KCl (3.0), $CaCl_2$ (2.0), $NaH_2PO_4$ (1.8), $MgCl_2$ $4H_2O$ (0.7).) The aorta was cannulated, and perfuse retrograde with Tyrode's solution. The perfusate (200 ml) was recirculated through a warming bath and filling pressure was adjusted to 20 cm of $H_2O$. Recirculation time was ~1 min, based on the time to decrease in left ventricular (LV) pressure following addition of $I_{Ca}$ blockers to the recirculating perfusate. Temperature was monitored using a thermistor probe positioned in the right ventricle (RV) and maintained at 33±1° C. by a closed loop feed back system. The perfusate was vigorously bubbled with 95% $O_2$, 5% $CO_2$ and pH was monitored throughout the experiments and adjusted to 7.4 with 1N NaOH or HCl, as appropriate. Both atria were removed and drains were placed in the RV and LV apices. An electrocardiogram (ecg) lead was sutured to the LV apex and the proximal pulmonary artery. Epicardial pacing wires were inserted into the RV free wall. Bradycardia was produced by crushing the AV node with a forceps. Epicardial pacing maintained a minimum cycle length of 1500 ms (heart rate of 40 beats/min). Pacing output was adjusted to twice diastolic threshold. In most experiments LV pressure was continuously monitored with a solid state transducer (Camino Laboratories) placed in a saline filled latex balloon. The balloon was secured with a purse string suture around the left atrial remnant and pressure was adjusted to maximize the LV developed pressure (LVDP) keeping the LV end diastolic pressure <10 mmHg. LVDP (peak systolic pressure—peak diastolic pressure) measurements are reported as the mean of 3 contiguous beats except during irregular rhythms and at EAD termination. During irregular rhythms LVDP measurement was reported as the mean of 3 beats following the longest interbeat intervals. LVDP is reported as the first beat without an EAD following $I_{Ca}$ blockade (FIG. 1C). LVDP stability was defined as <10% interbeat variability.

In most experiments a single MAP electrode (EP technologies Inc., Sunnyvale, Calif.) was positioned over the LV epicardium with a macro-manipulator. The heart was positioned against an adjustable stop opposite the epicardial MAP catheter to minimize heart motion. In a preliminary series of experiments designed to test the concordance of endocardial and epicardial EADs the LV balloon was omitted and paired MAP catheters were positioned opposite one another on the LV epicardial and endocardial free wall. MAP recordings were concordant for the presence and absence of EADs in all but one instance, suggesting that epicardial MAP recording is a valid method for detecting EADs from LV epicardium and endocardium in this isolated heart model. All MAP signals were amplified from (0 to 100 Hz) with a direct current coupled preamplifier (EP technologies Inc., Sunnyvale, Calif.) and recorded directly onto a chart recorder (Gould 2600S) at 100 mm/sec. Data from some experiments were digitized (Neuro-corder) and stored on a videotape recorder. Acceptable MAP catheter position was confirmed by a stable action potential configuration free of EADs or delayed after depolarizations (DADs) during a >10 minute control period. The MAP amplitude was defined as the difference between phase 2 and phase 4. MAP amplitude at the start of the experiments was 10.4 (±1.26) mV. The MAP duration was measured from the onset of phase 0 to the point of 50% ($APD_{50}$) and 90% ($APD_{90}$) repolarization. When present, EADs were included in the APD measurements. All MAP durations are reported as the mean of 3 contiguous beats, except following EAD termination where the first beat after EAD termination by $Cd^{2+}$ or nifedipine was used. Beat to beat intervals were measured from the onset of phase 0 using contiguous MAPs. Beat to beat intervals during irregular rhythms are reported as the longest intervals present during the measurement period.

EADs were defined as discrete oscillations in MAP repolarization with the slope of the tangent to the onset of the oscillation >0.0 (FIG. 1). EADs had to be present on most (>90%) beats over a 1 min period or in a stable bigeminal alternating pattern to be classified as inducible. Once these criteria were met EADs continued for >2 min and always required $I_{Ca}$ blockade for termination. Multiple EADs were defined as >1 EAD ocurring per beat (FIG. 1). The CaM kinase inhibition experiments consisted of 4 periods (FIG. 1A). The first period (>10 min) was the control and established stable baseline values for MAPs, LVDP, heart rate, and rhythm. The second period followed addition of KN-92 or KN-93 to the perfusate and lasted 10 min. The third period followed addition of clofilium to the perfusate and lasted for 30 min or until EADs occurred. If no EADs occurred then the longest MAP durations were used. MAP and LVDP measurements were made at 10 min intervals and at the time of EAD occurrence during the third period. The fourth period only consisted of experiments where prior EADs occurred, and measurements followed addition of nifedipine (10 µmol/l) or $Cd^{2+}$ (200–500 µmol/l) to the perfusate.

Example 2

Early Afterdepolarizations are Prevented by Pretreatment with the CaM kinase Inhibitor KN-93

We investigated if CaM kinase contributed to ventricular EAD initiation and maintenance, given its role in the enhancement of $I_{Ca}$. This was tested using the CaM kinase inhibitor KN-93, and its inactive analog KN-92. The decision to use KN-93 and KN-92 at 0.5 µmol/l was based on our finding that these agents were equally effective direct $I_{Ca}$ antagonists at this concentration (FIG. 6C).

Isolated hearts pretreated with the the CaM kinase inhibitor KN-93 (0.5 µmol/l) were significantly less likely to develop EADs in response to clofilium (7.5 µM) (EADs in 4/10 hearts) than hearts pretreated with the inactive analog KN-92 (EADs in 10/11 hearts) (0.5 µmol/l) (P=0.024). EAD induction by clofilium was not different in hearts pretreated with KN-92 (EADs in 10/11 hearts) compared to hearts without any type of pretreatment (EADs in 8/8 hearts), suggesting that the inactive analog KN-92 had no effect on EAD inducibility by clofilium (data not shown). When EADs were subclassified as single or multiple oscillations during MAP repolarization, multiple EADs :occurred more frequently in hearts pretreated with the inactive analog KN-92 (7/11) compared with those pretreated with the CaM kinase inhibitor KN-93 (1/10) (p=0.024). The differences in EAD inducibility in hearts pretreated with KN-93 and KN-92 were not due to differences in MAP duration (FIG. 3) or heart rate (FIG. 2). These findings suggest that KN-93 suppression of EADs is independent of known factors that facilitate EADs, such as heart rate and action potential duration.

Example 3

CaM Kinase Inhibition Prevented Increased Left Ventricular Developed Pressure During Action Potential Prolongation and Early Afterdepolarizations Left ventricular developed pressure increased significantly, compared with control, following addition of clofilium to the bath in hearts pretreated with the inactive. analog KN-92 (FIG. 2A). Left ventricular developed pressure increases occurred in step with MAP duration prolongation (FIG. 3) and EADs, but without a change in heart rate (FIG. 2B). KN-93 pretreatment completely prevented the increase in LVDP by clofilium (FIG. 2A) without reducing MAP duration prolongation (FIG. 3) or changing heart rate (FIG. 2B). Increased LVDP during MAP prolongation and EADs is likely due to CaM kinase—mediated $I_{Ca}$ augmentation.

Example 4

Figure 4:
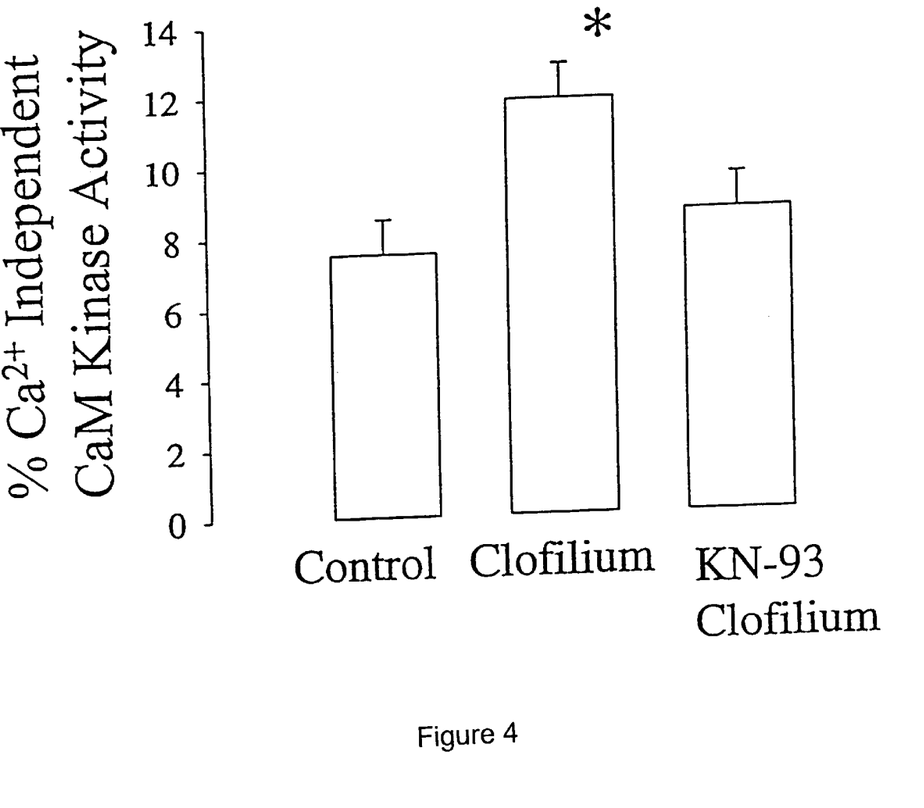

$Ca^{2+}$-Independent CaM Kinase Activity is Increased During Early Afterdepolarizations Once activated by increased $[Ca^{2+}]_i$ CaM kinase II activity becomes $Ca^{2+}$-independent via intersubunit phosphorylation. Thus, $Ca^{2+}$-independent CaM kinase activity is a marker for CaM kinase activation. Because EADs appear due to $I_{Ca}$ in this isolated heart model, we hypothesized that EADs are associated with increased $Ca^{2+}$-independent CaM kinase activity. $Ca^{2+}$-independent CaM kinase activity increased significantly in hearts demonstrating EADs after clofilium compared to hearts without clofilium treatment or EADs (FIG. 4). No significant increase in $Ca^{2+}$-independent CaM kinase activity occurred, compared to control, in hearts pretreated with KN-93 (0.5 µmol/l) prior to clofilium (FIG. 4). These findings show that EADs are associated with an increase in $Ca^{2+}$-independent CaM kinase activity and that the concentration of KN-93 used to suppress EADs in these experiments is sufficient to significantly inhibit CaM kinase activation. This increase in $Ca^{2+}$-independent CaM kinase activity is consistent with the hypothesis that CaM kinase is a proarrhythmic signaling molecule for EADs.

Example 5

KN-93 inhibits CaM Kinase Activity in Rabbit Myocardium

Figure 5:
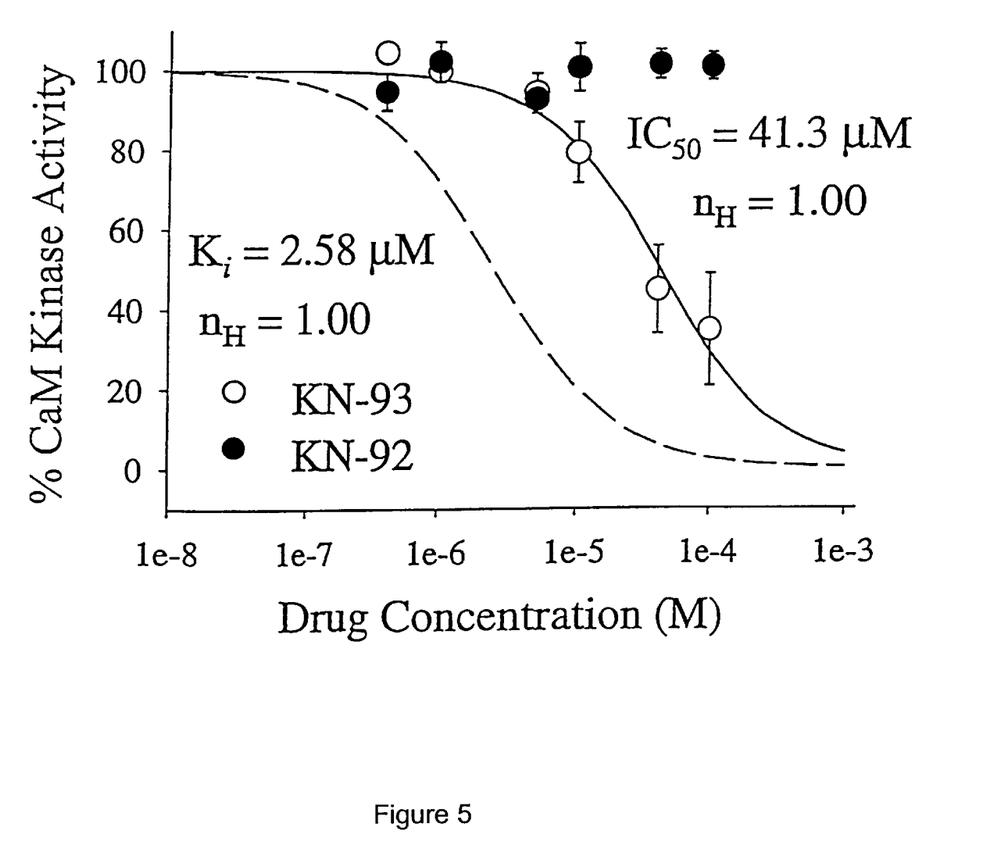
Figure 6:
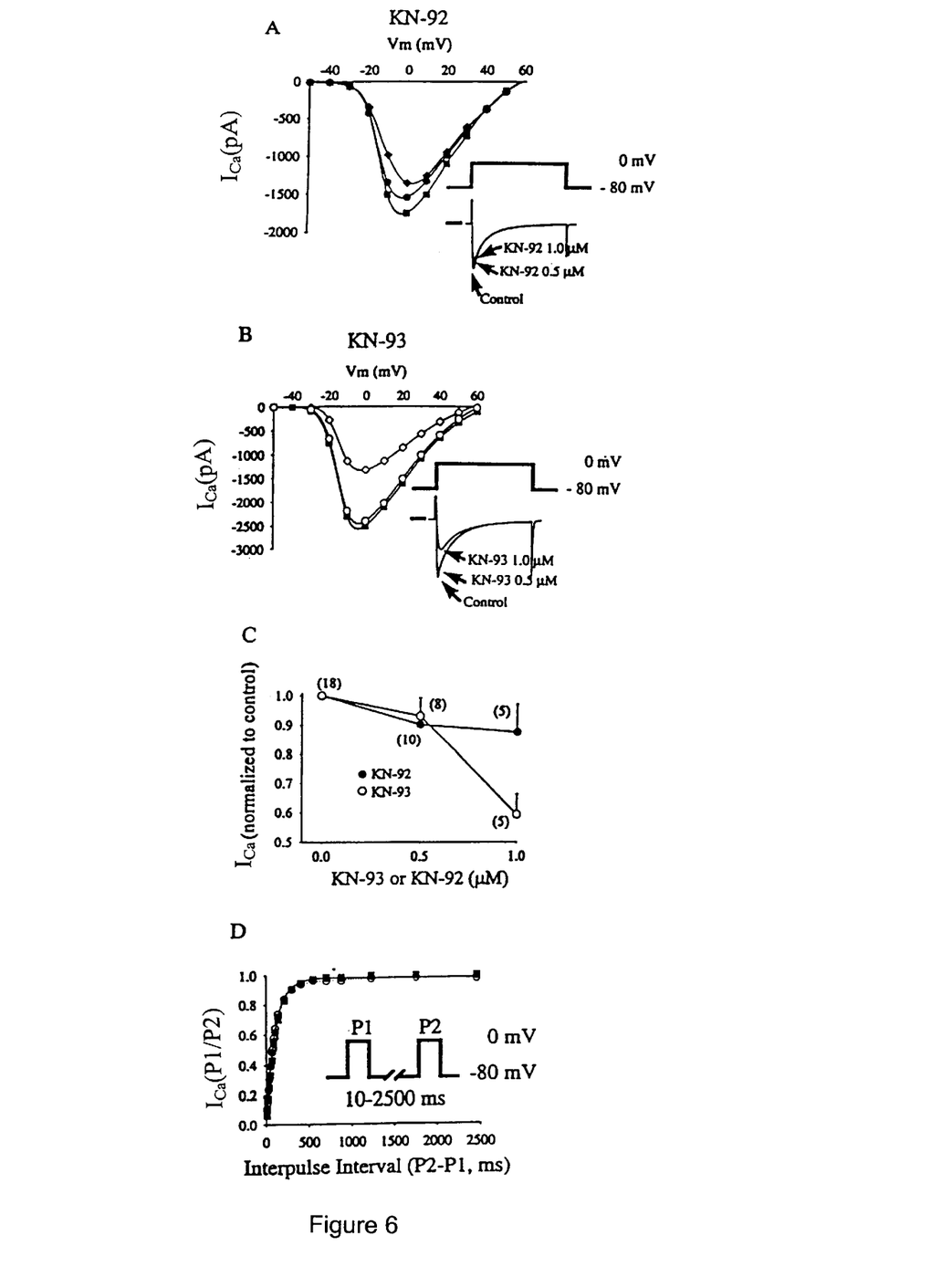

In vitro measurements of CaM kinase activity in LV tissue homogenate show that KN-93 is an inhibitor of CaM kinase with a $K_i$, <2.58 µmol/l (FIG. 5). The inactive analog KN-92 did not cause appreciable inhibition of CaM kinase activity. These findings are similar to earlier findings reported in rat pheochromocytoma (PC12) cells. These results show that KN-92 is a valid control for CaM kinase inhibition by KN-93.

Experimental Methods

Left ventricular homogenate was prepared as follows: after removal of the heart, it was placed in nominally $Ca^{2+}$ free ice-cold HEPES-buffered Tyrode's solution. One to two grams of the left ventricular free wall was cut away, coarsely minced, and suspended in 5–10 ml of cold homogenization buffer (mmol/l: 20 PIPES, 1 EDTA, 1 EGTA, 2 DTT, 10 sodium pyrophosphate, and 50–100 µg/ml leupeptin) at pH 7.0. Tissue suspension was homogenized at 4° C. using 3–10 sec bursts of a Polytron with 30 sec pauses in between bursts. The homogenate was then centrifuged at ~10,000×g for 20 min at 4° C. using a JA-20 rotor. The supernate was removed and used directly in the assay. Protein concentration was measured by the method of Bradford, using BSA as the standard.

Assay of CaM kinase activity was performed essentially as described by Waldmann et al. with a few modifications. The assay was performed in triplicate in a final volume of 50 µl containing 50 mmol/l PIPES, pH 7.0, 10 mmol MgCl2, 0.1 mg/ml BSA, 10 µmol/l autocamtide 3 (synthetic kinase substrate), 150 µmol/l calmodulin, 1 mmol/l $CaCl_2$ or 1 mmol/l EGTA, and increasing concentrations (0–100 µmol/l) of KN-93 or KN-92. 30–50 µg of tissue homogenate were added per assay tube, and samples were then pre-incubated at 30° C. for 1 min. The kinase reaction was then started by addition of 50 µmol/l (final) $\gamma^{32}P$-ATP (~400 cpm/pmol), and incubation was carried out for an additional 1 to 2 minutes. The reaction was terminated by addition of 10 µl cold trichloroacetic acid (30% w/v), and samples were then placed on ice for $\geq 2$ min. Calcium/calmodulin-dependent phosphorylation of the autocarntide 3 substrate was then quantitated as described. Calcium/calmodulin-independent CaM kinase activity was quantitated as described above, but $Ca^{2+}$ was omitted from the assay solution. Data describing inhibition of CaM kinase activity by KN-93 was fit according to the Hill equation.

Example 6

KN-92 and KN-93 are Equipotent Direct Blockers of L-Type $Ca^{2+}$ Current

We assessed the relative L-type $Ca^{2+}$ current ($I_{Ca}$) blocking potency of KN-92 and KN-93 in single ventricular myocytes using whole cell voltage clamp methodology. These studies were performed because of the observation that clofilium-induced EADs are terminated by $I_{Ca}$ blockade in isolated rabbit hearts, along with findings that other CaM kinase inhibitory agents block $I_{Ca}$. Since CaM kinase is known to enhance $I_{Ca}$, we attempted to block CaM kinase activation by dialyzing cells, via the recording micropipette, with the fast $Ca^{2+}$ chelator BAPTA (20 mmol/l), so that only direct effects of KN-92 and KN-93 on $I_{Ca}$ were measured. External application of either KN-92 (0.5 µmol/l) or KN-93 (0.5 µmol/l) caused equipotent steady state inhibition of peak $I_{Ca}$ (36.2±1.9%, KN-92 and 36.2±4.3% KN-93) in isolated rabbit ventricular myocytes (FIG. 5). Estimated $IC_{50}$ values were ~1 µmol/l for both drugs. Neither KN-92 or KN-93 shifted the apparent voltage dependence of $I_{Ca}$ activation. The amount of $I_{Ca}$ inhibition by 0.5 µmol/l KN-92 or KN-93 is apparently insufficient to suppress EADs in this model (Example 2). These results show that KN-92 is a valid control for the direct $I_{Ca}$ blocking effects of KN-93 in the isolated rabbit ventricular myocytes because these agents have equivalent $I_{Ca}$ antagonist effects at the concentration (0.5 µmole/l) used to suppress EADs (FIG. 6C).

Experimental Methods

Single ventricular myocytes were prepared as previously described in Anderson et al. (1994) *Circ Res*, 75:854–861. The standard $Ca^{2+}$ containing solution for myocyte preparation was composed of(mmol/l) NaCl 137.0, HEPES (free acid) 10.0, $NaH_2PO_4$ 0.33, glucose 10.0, KCl 5.4, $CaCl_2$ 1.8, and $MgCl_2$ 2.0. The nominally $Ca^{2+}$ free solution was identical, except $CaCl_2$ was omitted. The low $Ca^{2+}$ solution contained 0.2 mmol/l $CaCl_2$. The collagenase solutions were prepared with 1% BSA (wt/vol) and ~60 U/ml collagenase (Worthington Biochemicals) and ~0.1 U/ml type XIV protease (Sigma Chemical Co). The myocyte bath solution contained (mmol/l) NaCl 137.0, CsCl 20.0, glucose 10.0, HEPES 10.0, KCl 5.4, $CaCl_2$ 1.8, $MgCl_2$ 0.5, and tetrodotoxin 0.03; pH was adjusted-to 7.4 with 10N NaOH. The intracellular pipette solution contained (mmol/l) CsCl 130.0, 4Cs BAPTA 10.0 (Molecular Probes), phosphocreatine 5.0, NaGTP 1.0, and MgATP1.0; pH was adjusted to 7.2 with 10N CsOH.

New Zealand White rabbits (2 to 3 kg body weight) were killed by pentobarbital (50 mg/kg IV) overdose. Hearts were rapidly excised and placed in ice cold nominally $Ca^{2+}$ free HEPES—buffered myocyte bath solution. The aorta was cannulated, and the heart was perfused in a retrograde fashion with a nominally $Ca^{2+}$ free perfusate for 15 minutes at 37° C. This was followed by a 15-min perfusion with collagenase—containing nominally $Ca^{2+}$ free solution. Final perfusion was with collagenase—containing low $Ca^{2+}$ (0.2 mmol/L) solution. The LV and septum were cut away, coarsely minced, and placed in a beaker containing low $Ca^{2+}$ solution with 1% (wt/vol) bovine serum albumin (BSA) at 37° C. Myocytes were dispersed by gentle agitation, collected in serial aliquots, and then maintained in standard saline solution containing 1.8 mmol/L $Ca^{2+}$. All solutions were vigorously oxygenated.

Isolated quiescent ventricular myocytes were studied with patch-clamp methodology in the whole cell recording configuration by using an Axopatch 1B amplifier (Axon Instruments). Micropipettes were pulled from glass capillary tubing (VWR) and heat-polished to a tip resistance of 1–3 MΩ when filled with the intracellular solution.

The cell membrane was commanded from −40 mV to +60 mV for 200 ms in 10 mV steps from a holding potential of −40 mV at a stimulation of 1.0 Hz. This protocol was repeated with 60 sec pauses between series of voltage clamp steps, and transmembrane current was sampled at 2 kHz. Voltage clamp protocols and data acquisition were performed using PCLAMP software (version 6.0, Axon Instruments) on a microcomputer (Gateway 2000) with a A/D, D/A convertor (Digidata 1200, Axon Instruments). All experiments were performed at room temperature (20° C. to 23° C.) on the stage of a Diaphot inverted microscope (Nikon corp). Pure macroscopic $I_{Ca}$ is observed under these recording conditions. Rapid intracellular $Ca^{2+}$ buffering with BAPTA (10 mmol/l) and the long (60 sec) rests between voltage step protocols were chosen to minimize CaM kinase activation so direct $I_{Ca}$ blockade by KN-93 or KN-92 was measured, independent of an effect on CaM kinase. Peak $I_{Ca}$ stability was defined when peak $I_{Ca}$ varied <10% between voltage steps. Direct $I_{Ca}$ blockade by KN-92 or KN-93 was examined after a stable control period. KN-92 or KN-93 was added to the bath at increasing concentrations. Peak $I_{Ca}$ stability was established before changing to the next KN-92 or KN-93 concentration.

Example 7

Early Afterdepolarizations are Also Prevented by Pretreatment with Highly Specific CaM Kinase Inhibitory Peptides Experiments performed in isolated rabbit heart cells using highly specific CaM kinase inhibitory peptides further corroborated the results obtained using the inhibitor KN-93 (Examples 2 and 3). The peptide of the sequence KKAL-HRQEAVDCL (SEQ ID NO:1) had been previously reported to inhibit CaM kinase, but not PKA or PKC. A second peptide, KKALHAQERVDCL (SEQ ID NO:2), which does not inhibit CaM kinase was used as a control.

Action potentials were induced in isolated rabbit ventricular myocytes studied in current clamp with low (1.0 mM) extracellular potassium to favor EAD induction. EADs were induced in the majority of control cells dialyzed with an inactive peptide (11/15) but not in cells dialyzed with the CaM kinase inhibitory peptide (4/15). EADs seen in cells treated with the control peptide tended to be complex and repetitive (i.e. multiple), but only single EADs were present in inhibitory peptide treated cells.

Furthermore, measurements of the L-type calcium window current using a prolonged EAD—containing action potential as a voltage clamp wave form revealed that an increase in the current was prevented by dialysis with the CaM kinase inhibitory peptide (data not shown). The control peptide had no significant effect on this calcium current. These results are consistent with the augmentation of arrhythmogenic L-type calcium window current by CaM kinase.

Example 8

Inward Currents Associated with Delayed Afterdepolarizations and Intracellular Calcium Overload are Suppressed by CaM Kinase Inhibition.

Isolated heart cells (Experimental Methods, Example 6) were stimulated (0.5 Hz) in voltage clamp using a prolonged action potential wave form (FIG. 7A). Rapid pacing favors intracellular calcium overload. Inward currents that develop in response to rapid pacing are a marker for intracellular calcium overload and they are the basis for arrhythmogenic delayed afterdepolarizations (DADs). The majority of cells (5/6) treated with an inactive control peptide (SEQ ID NO:2) developed inward currents (FIG. 7B). Treatment of a second group with the active CaM kinase inhibitory peptide (SEQ ID NO:1) completely prevented the inward currents (inward currents in 0/5 cells) (FIG. 7C). Ryanodine (10 µmole/l), prevents intracellular calcium overload by blocking release of calcium from intracellular stores, also prevented development of pacing induced inward currents (in 2/2 cells tested). These results indicate that CaM kinase inhibition can prevent intracellular calcium overload and development of DAD—linked currents.

Experimental Methods

Action potential recording was performed in the following bath solution (mmol/L): NaCl 140.0, Glucose 10.0, HEPES 5.0, KCl 5.4, $CaCl_2$ 2.5, $MgCl_2$ 1.0; pH was adjusted to 7.4 with 10 N NaOH. The intracellular-pipette solution for action potential recording contained (mmol/L): K aspartate 120.0, HEPES 10.0, EGTA 10.0, $Na_2ATP$ 5.0, $MgCl_2$ 4.0, $CaCl_2$ 3.0; pH was adjusted to 7.2 with 1N KOH. Unless otherwise noted, all chemicals were from Sigma.

Cells were stimulated at 0.1 Hz in whole cell configuration in current clamp mode with 0.1 to 1.0 nA pulses of depolarizing current (1.25×threshold) for 2–3 ms at room temperature (20–23° C.). Action potentials were low pass filtered at 2 KHz and sampled at 2.5 KHz with a 12-bit analog to digital converter (Digidata 1200 B, Axon Instruments). A long action potential waveform was digitized and stored for application as a voltage command using pClamp 6.03.

Isolated cells were studied with the action potential command wave form using voltage clamp methodology (Experimental Methods, Example 6). Cells were stimulated at 0.5 Hz and 32° C. (heated stage from Warner Instruments) for up to 100 beats. Recording solutions were identical to those for action potential recording except that the calcium buffer EGTA was omitted from the intracellular solution to favor intracellular calcium overload. The presence or absence of the post-repolarization inward current was noted.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for treating arrhythmia in a human subject comprising the administration of a direct inhibitor of a multifunctional $Ca^{2+}$/calmodulin-dependent protein kinase in an amount sufficient to suppress early afterdepolarizations, delayed afterdepolarizations, or intracellular calcium overload.

2. A method of claim 1, wherein said inhibitor is a CaM kinase II inhibitor.

3. A method of claim 1, wherein said inhibitor is 2[N-(2hydroxyethyl)-N-(4-methoxy-benezenesulfonyl)]-amino-N-(4-chlorocinnamyl)-N-methylbenzylamine.

4. A method of claim 1, wherein said inhibitor is the peptide of the sequence KKALHRQEAVDCL (SEQ ID NO:1).

5. A method of claim 1, wherein said administration is by a means selected from the group consisting of intravenous infusion, parenteral pump infusion, transcutaneous administration, intracoronary artery infusion, and intrapericardial infusion.

6. A method of claim 1, wherein said arrhythmia is ventricular tachycardia.

7. A method of claim 1, wherein said arrhythmia is ventricular fibrillation.

8. A method of claim 1, wherein said arrhythmia is atrial fibrillation.

9. A method of claim 1, wherein said inhibitor is administered in a dose of from about 0.05 mg to about 5.0 mg per kilogram of body weight.

10. A method of claim 1, wherein said inhibitor is administered in a dose of from about 0.3 mg to about 3.0 mg per kilogram of body weight.

11. A method of claim 1, wherein said method further comprises the administration of an effective amount of a second antiarrhythmic agent.

12. A method of claim 11, wherein said second antiarrhythmic agent is a potassium channel antagonist.

13. A method of claim 11, wherein said second antiarrhythmic agent is selected from the group consisting of a potassium channel blocker, β adrenergic receptor antagonist, and a calcium channel blocker.

14. A method of claim 1, wherein said method further comprises treatment with an antiarrhythmic device.

15. A method of claim 14, wherein said antiarrhythmic device is selected from the group consisting of a permanent pacing system, an atrial implantable cardioverter defibrillator, and a ventricular implantable cardioverter defibrillator.

16. A method for preventing arrhythmia in a human subject comprising the administration of a direct inhibitor of a multifunctional $Ca^{2+}$/calmodulin-dependent protein kinase in an amount effective to suppress early afterdepolarizations, delayed afterdepolarizations, or intracellular calcium overload.

17. A method of claim 16, wherein said inhibitor is a CaM kinase II inhibitor.

18. A method of claim 16, wherein said inhibitor is 2[N-(2hydroxyethyl)-N-(4-methoxy-benezenesulfonyl)]-amino-N-(4-chlorocinnamyl)-N-methylbenzylamine.

19. A method of claim 16, wherein said inhibitor is the peptide of the sequence KKALHRQEAVDCL (SEQ ID NO:1).

20. A method of claim 16, wherein said administration is by a means selected from the group consisting of intravenous infusion, parenteral pump infusion, transcutaneous administration, intracoronary artery infusion, and intrapericardial infusion.

21. A method of claim 16, wherein said arrhythmia is ventricular tachycardia.

22. A method of claim 16, wherein said arrhythmia is ventricular fibrillation.

23. A method of claim 16, wherein said arrhythmia is atrial fibrillation.

24. A method of claim 16, wherein said inhibitor is administered in a dose of from about 0.05 mg to about 5.0 mg per kilogram of body weight.

25. A method of claim 16, wherein said inhibitor is administered in a dose of from about 0.3 mg to about 3.0 mg per kilogram of body weight.

26. A method of claim 16, wherein said method further comprises the administration of an effective amount of a second antiarrhythmic agent.

27. A method of claim 26, wherein said second antiarrhythmic agent is a potassium channel antagonist.

28. A method of claim 26, wherein said second antiarrhythmic agent is selected from the group consisting of a potassium channel blocker, a β adrenergic receptor antagonist, and a calcium channel blocker.

29. A method of claim 16, wherein said method further comprises treatment with an antiarrhythmic device.

30. A method of claim 29, wherein said antiarrhythmic device is selected from the group consisting of a permanent pacing system, an atrial implantable cardioverter defibrillator, and a ventricular implantable cardioverter defibrillator.

31. A method for treating arrhythmia in a human subject, wherein said method comprises directly decreasing the $Ca^{2+}$/calmodulin-dependent kinase activity level in said subject.

32. A method of claim 31, comprising the administration of a $Ca^{2+}$/calmodulin-dependent kinase inhibitor to said subject.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 13 amino acids
      (B) TYPE: amino acid
      (C) STRANDEDNESS:
      (D) TOPOLOGY: linear    (ii) MOLECULE TYPE: peptide    (iii) HYPOTHETICAL: NO    (iv) ANTI-SENSE: NO

```
            (x) PUBLICATION INFORMATION:
                (A) AUTHORS: Braun, Andrew P.
                    Schulman, Howard
                (C) JOURNAL: Journal of Physiol
                (D) VOLUME: 488
                (F) PAGES: 37-55
                (G) DATE: 1995
                (K) RELEVANT RESIDUES IN SEQ ID NO:1: FROM 1 TO 13

(xi) SEQUENCE DESCRIPTION: SEQ ID NO:1:

Lys Lys Ala Leu His Arg Gln Glu Ala Val Asp Cys Leu
1               5                   10

(2) INFORMATION FOR SEQ ID NO:2:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (x) PUBLICATION INFORMATION:
            (A) AUTHORS: Braun, Andrew P.
                Schulman, Howard
            (C) JOURNAL: Journal of Physiol
            (D) VOLUME: 488
            (F) PAGES: 37-55
            (G) DATE: 1995
            (K) RELEVANT RESIDUES IN SEQ ID NO:2: FROM 1 TO 13

(xi) SEQUENCE DESCRIPTION: SEQ ID NO:2:

Lys Lys Ala Leu His Ala Gln Glu Arg Val Asp Cys Leu
1               5                   10
```